(12) United States Patent
Faupel et al.

(10) Patent No.: US 7,041,057 B1
(45) Date of Patent: May 9, 2006

(54) TISSUE INTERFACE DEVICE

(75) Inventors: Mark L. Faupel, Alpharetta, GA (US);
Krishna Kumar, Duluth, GA (US); J. David Farquhar, Commerce, GA (US);
Mark Vreeke, Suwanee, GA (US);
Alan Smith, Atlanta, GA (US);
Michael Hatch, Sugar Hill, GA (US);
Teresa Woods, Atlanta, GA (US)

(73) Assignee: SpectRx, Inc., Norcross, GA (US)

( * ) Notice: Subject to any disclaimer, the term of this patent is extended or adjusted under 35 U.S.C. 154(b) by 252 days.

(21) Appl. No.: 10/130,686

(22) PCT Filed: Nov. 17, 2000

(86) PCT No.: PCT/US00/31765

§ 371 (c)(1),
(2), (4) Date: Sep. 11, 2002

(87) PCT Pub. No.: WO01/35820

PCT Pub. Date: May 25, 2001

Related U.S. Application Data

(60) Provisional application No. 60/166,481, filed on Nov. 19, 1999, provisional application No. 60/178,148, filed on Jan. 26, 2000, provisional application No. 60/244,568, filed on Oct. 31, 2000.

(51) Int. Cl.
*A61B 5/00* (2006.01)
*A61B 5/05* (2006.01)
*A61B 5/04* (2006.01)

(52) U.S. Cl. ............... 600/365; 600/354; 600/345; 600/387; 600/362; 600/366; 600/352

(58) Field of Classification Search ............... 600/309, 600/345–347, 348, 352–354, 361–366, 387, 600/391, 573, 578, 580, 583
See application file for complete search history.

(56) References Cited

U.S. PATENT DOCUMENTS 4,627,445 A * 12/1986 Garcia et al. ............... 600/583

(Continued)

FOREIGN PATENT DOCUMENTS

WO    WO 99/44507    9/1999

(Continued)

*Primary Examiner*—Max F. Hindenburg
*Assistant Examiner*—Navin Natnithithadha
(74) *Attorney, Agent, or Firm*—Altera Law Group, LLC

(57) ABSTRACT

A tissue interface device (10) suitable for positioning on or about one or more artificial openings in a biological membrane of an organism and for coupling to a monitor and control unit and a vacuum source. The tissue interface device (10) comprises a housing (100), a sensor channel (130), and a sensor (150). The housing (100) defines an orifice (120), the orifice (120) having an open inlet port (122) on the bottom end (102) of the housing (100) and a distal end (124) that is in fluid communication with the sensor channel (130). The orifice (120) is in fluid communication with fluid that flows from the artificial opening formed in the biological membranes. The sensor channel (130) is for coupling to, and fluid communication therewith, the vacuum source. The sensor (150) is positioned in the sensor channel (130) in a flow path of the fluid for sensing a characteristic of the fluid as it flows out from the artificial opening. The sensor generates a sensor signal representative thereof.

26 Claims, 8 Drawing Sheets

U.S. PATENT DOCUMENTS 5,474,065 A * 12/1995 Meathrel et al. ............ 600/376
5,882,317 A      3/1999 Saito et al.
6,048,337 A *  4/2000 Svedman .................... 604/313
6,071,249 A *  6/2000 Cunningham et al. ...... 600/578
6,071,251 A *  6/2000 Cunningham et al. ...... 600/584
6,117,290 A *  9/2000 Say et al. ................... 600/352
6,138,044 A * 10/2000 Svedman .................... 600/387

FOREIGN PATENT DOCUMENTS

WO      WO 99/58050      11/1999

* cited by examiner

TISSUE INTERFACE DEVICE

This application claims priority to U.S. Provisional Application No. 60/166,481 filed Nov. 19, 1999; U.S. Provisional Application No. 60/178,148 filed Jan. 26, 2000; and U.S. Provisional Application No. 60/244,568 filed Oct. 31, 2000.

BACKGROUND OF THE INVENTION

1. Field of the Invention

The present invention relates to tissue interface devices, and more particularly to a tissue interface device wherein fluid is extracted from a biological tissue and placed into contact with a sensor for sensing a characteristic of the fluid flowing from an artificial opening in a biological membrane.

2. Background Art

Monitoring systems that sample and measure characteristics of fluids from a biological tissue, such as on a human, are well known. Many of these systems involve implanting sensors and related devices into the organism (such as under the skin) in order to obtain fluid samples and make measurements of those samples. Implanted sensors, in addition to the pain caused to the organism during the implantation of the sensor, degrade rapidly when introduced into the organism. Even for short term implants, it has been shown that within the first several hours after implantation a rapid deposition of fibroblasts, macrophage plaques, fibrogen growth and other natural physiological encapsulation processes surround the implant and thereby impair, restrict, and modify, in a dynamic fashion, the free flow of the analytes of interest into the active sensor region of the implanted device.

Alternatively, fluids may be drawn from the biological membrane of the organism through the use of needle or cannula that penetrate deep into the membrane (such as penetrating deep into the dermis or subcutaneous tissue of a human). The extracted fluid is drawn toward a remote sensor or sensor array for measurement of the desired characteristic. This solution requires a large volume of fluid be drawn before the fluid reaches the sensor. Further, this solution can have detrimental effects on the measurement of a desired current analyte concentration level because of the lag time imposed by the large inherent time delay required for the fluid to reach the sensor from the point of fluid withdrawal. Because of the lag time, approximation techniques must be applied to provide a more time-accurate indication of the current concentration of the desired analyte in the fluid.

SUMMARY OF THE INVENTION

Briefly, according to one aspect, the present invention is directed to a tissue interface device for extracting biological fluid from a biological tissue and for sensing a characteristic of the fluid. The tissue interface device is suitable for positioning on or about the surface of the biological membrane of the biological tissue and is adapted to be removably coupled to a remote monitor and control unit and a vacuum source. The tissue interface device comprises a housing that defines an orifice having an open inlet port on a bottom end of the housing to receive fluid and an opposing distal end. In use, the orifice of the housing is in fluid communication with fluid produced from one or more artificial openings formed in the biological membrane.

The housing also has a sensor channel and a sensor. The sensor channel is in fluid communication with the distal end of the orifice. The sensor is positioned in the sensor channel and in a flow path of the fluid for continuously sensing a characteristic of the fluid as it is produced from the artificial opening, and generates a sensor signal representative thereof.

The present invention involves positioning the sensor ex vivo, proximate the surface of the organism, and coupling the sensor to the organism via the fluid conducting tapered orifice of the housing. Consequently, oxygen (if necessary) to support the sensor reaction is readily available, allowing for a simpler basic array design, higher signal-to-noise ration, faster response, better linear tracking of the physiological changes in an analyte of interest, and longer life of the sensor. By keeping all of the foreign material of the tissue interface device outside of the body, the auto-immune derived encapsulation and rejection responses naturally occurring with any implanted device never begin.

Further, by avoiding actual penetration of the body to insert a sensor, needle, or cannula, a significant disadvantage of the prior art devices and methods is obviated by the tissue interface device of the present invention. Also, risks of infection that are present in the prior art systems are dramatically reduced in connection with the present invention because neither sensor implantation is involved nor a membrane breaching connection to a needle or cannula.

Still further, the tissue interface device of the present invention provides for high interstitial fluid flux rates without causing increased erythema that may prolong skin healing. Additionally, by minimizing the dead volume between the artificial opening in the membrane and the sensor, and hence minimizing the lag time, a further significant disadvantage of the prior art systems and method is obviated by the device of the present invention.

The present invention is useful in a system that performs a single (one time) measurement of an analyte in a biological fluid of an organism from a tissue interface device placed in contact with the biological membrane, as well as in a system that continually monitors an analyte from an organism from such a tissue interface device. Thus, it is contemplated that an analyte in a biological fluid of an organism may be repeatedly assayed at regular and frequent intervals.

The above and other objects and advantages of the present invention will become more readily apparent when reference is made to the following description taken in conjunction with the accompanying drawings.

DETAILED DESCRIPTION OF THE INVENTION

Figure 1:
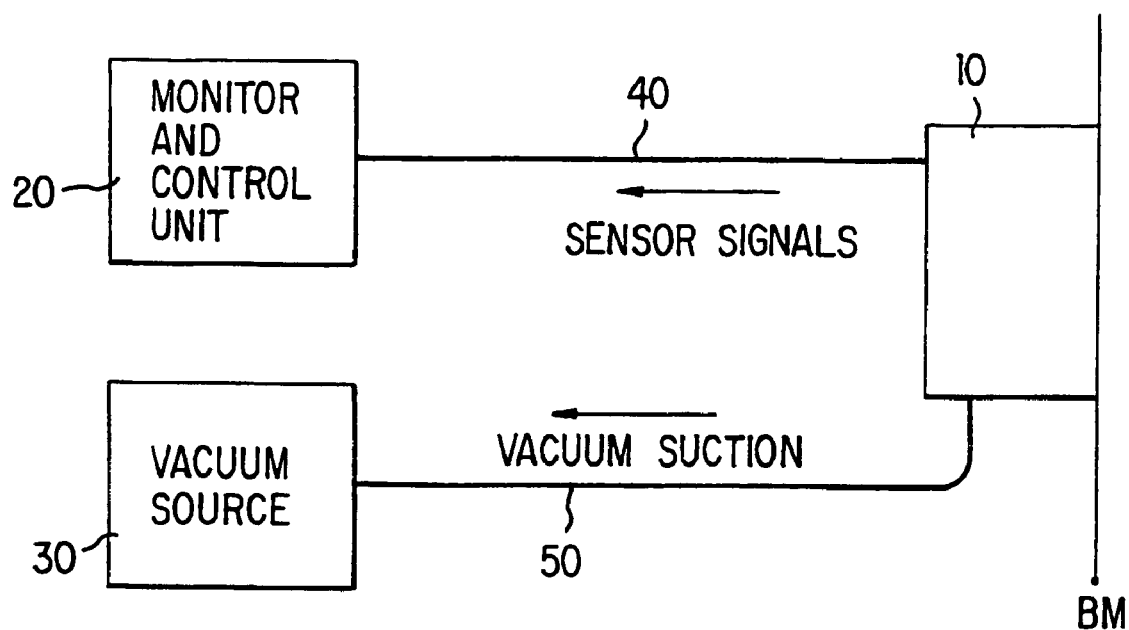
FIG. 1 is a block diagram generally showing an tissue interface device according to the present invention coupled to a monitor and control unit and a vacuum source.

The present invention may be understood more readily by reference to the following figures and their previous and following description, in which like numbers indicate like parts throughout the figures. It is to be understood that this invention is not limited to the specific devices described, as specific device components as such may, of course, vary. It is also understood that the terminology used herein is for the purpose of describing particular embodiments only and is not intended to be limiting.

As used in this specification and the appended claims, the singular forms "a," "an" and "the" may mean one or more than one. For example, "a" sensor may mean one sensor or more than one sensor.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment.

As used herein, the term "biological membrane" means the structure separating one area of an organism from another area of the organism, such as a capillary wall, or the outer layer of an organism which separates the organism from its external environment, such as skin, buccal mucosa or other mucous membrane.

As used herein, the term "suction" or "pressure" relates to the relative pressure as compared to the internal pressure of the organism to which the system is interfaced. "Vacuum" is used synonymously with the term "suction."

As used herein, the term "biological fluid" means blood serum, whole blood, interstitial fluid, lymph fluid, spinal fluid, plasma cerebrospinal fluid, urine, prostatic fluid, bile, pancreatic secretions, or any combination of these fluids. Other fluids that may be harvested from the surface of various tissues include, but are not limited to, fluids selected from the group consisting of mucus, saliva, breast milk, tears, gastric secretions and perspiration.

As used herein, "artificial opening" means any physical breach of the biological membrane of a suitable size for delivering or extraction fluid therethrough, including micropores.

As used herein, "poration," "microporation," or any such similar term means the artificial formation of a small hole, opening or pore to a desired depth in or through a biological membrane, such as skin or mucous membrane, or the outer layer of an organism to lessen the barrier properties of this biological membrane to the passage of biological fluids, such as analytes from within the biological membrane or the passage of permeants or drugs from without the biological membrane into the body for selected purposes, or for certain medical or surgical procedures. The size of the hole or "micropore" so formed is approximately 1000 micrometers in diameter.

As used herein, "monitor and control unit" means a device or devices suitable for being coupled to the tissue interface device of the present invention. The monitor and control unit includes means of receiving a sensor signal from the tissue interface device indicative of a characteristic of fluid flowing from an artificial opening in the biological membrane and deriving a measurement of a characteristic of the fluid. The monitor and control unit may also supply and/or control a vacuum source for coupling to the tissue interface device. The monitor and control unit may comprise a unified system (such as a single unit) or may be separate systems (such as a monitor and a control unit) interconnected as known in the art. The monitor and control unit may be designed for one time, i.e., discrete use, or may be designed to be placed in contact with the tissue for longer periods of time, e.g., hours, days or weeks, for periodic, continual or continuous analyte monitoring. An example of a monitor and control unit is disclosed in commonly assigned International Application No. PCT/US99/16378, entitled "System and Method for Continuous Analyte Monitoring," filed Jul. 20, 1999, which is incorporated herein by reference.

The term "continuously" or "continually" means acting on an ongoing basis at a frequency or event rate that may vary depending on a particular application. For example, the output of the sensor may be read on a periodic basis, such as every minute, several minutes, hour, several hours, etc. Moreover, at each reading event, the sensor output is optionally sampled multiple times, so as to obtain a plurality of readings relatively close in time, whereby an average or other adjustment of those multiple readings is made for determining a final reading that is displayed or logged.

As used herein, "analyte" means any chemical or biological material or compound suitable for passage through a biological membrane by the technology taught in this present invention, or by technology previously known in the art, of which an individual might want to know the concentration or activity inside the body. Glucose is a specific example of an analyte because it is a sugar suitable for passage through the skin, and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, and the like.

FIG. 1 illustrates one embodiment of system comprising a tissue interface device 10 and a monitor and control unit 20 having a vacuum source 30. The tissue interface device 10 is provided for use in an analyte monitoring system, which may operate on a continuous, continual and/or discrete basis. The tissue interface device 10 is operatively coupled, via an electrical umbilical cord 40 and a vacuum line 50, to the monitor and control unit 20 and the vacuum source 30. The electrical umbilical cord 40 provides electrical and optionally optical communication between the monitor and control unit 20 and the tissue interface device 10. Alternatively, the electrical umbilical cord 40 can be replaced by a wireless link in which case the monitor and control unit 20 and the tissue interface device 10 would each have a suitable transceiver to communicate over the wireless link. The vacuum line 50 provides mechanical communication between the vacuum source 30 and the tissue interface device 10. Generally, the function of the tissue interface device 10 is to attach to the surface of the biological membrane (BM) of the organism, collect fluid from the organism, and obtain a measurement of a characteristic of the fluid. The tissue interface device 10 ultimately produces an electrical signal that is indicative of a presence of concentration of an analyte. The tissue interface device 10 is composed of inexpensive materials and components and is designed to be disposable.

Referring to FIGS. 2–6, a first embodiment of the tissue interface device 10 according to the present invention is shown. In this embodiment, the tissue interface device 10 comprises a housing 100 that defines an orifice 120. The orifice 120 has an open inlet port 122 on a bottom end 102 of the housing to receive fluid from one or more artificial openings (O) in a biological membrane. The orifice 120 terminates at a distal end 124. The inlet port 122 has a first diameter D and the distal end 124 has a second diameter d. The orifice 120 may be tapered so that the second diameter d is less than the first diameter D. The orifice 120 may be shaped such that it closely conforms to the biological membrane when vacuum is applied to the biological membrane.

The housing 100 of the present invention also has a sensor channel 130 and a sensor 150. The sensor channel 130 is in fluid communication with the distal end 124 of the orifice and has an outlet port 132 for discharging fluid. The outlet port 132 is suitable for connection to the vacuum source 30. The sensor 150 is positioned in the sensor channel 130 and in a flow path of the fluid for sensing a characteristic of the fluid as it is produced from the artificial opening in the biological membrane. In one example, the sensor 150 is positioned proximate the distal end 124 of the orifice 120 to minimize the effective dead volume of the device between the distal end 124 of the orifice 120 and the sensor 150. The sensor 150 generates an electrical sensor signal representing the characteristic of the biological fluid.

The tissue interface device 10 may also comprise an electrical connector 160 and an electrical lead line 162. The electrical lead line 162 is in operative communication with the sensor 150 and couples the electrical sensor signal to the electrical connector 160. The electrical connector 160 is complementarily shaped so that it can be removably connected to an electrical umbilical cord 40 of the monitor and control unit 20.

It will be appreciated from the above that, in operation, the tissue interface device 10 is positioned on a site overlying one or more artificial openings in the biological membrane. The openings in the membrane may be made by a variety of means, such as those disclosed in commonly assigned U.S. Pat. No. 5,885,211. When positioned, the orifice 120 of the housing 100 is positioned in fluid communication with fluid produced from the artificial opening formed in the biological membrane. Fluid enters the tissue interface device 10 through the inlet port 122 and/or orifice 120. Under application of vacuum (V) at the outlet port 132, the surface of the biological membrane is drawn therein the orifice 120 and fluid is drawn from the artificial opening into the orifice 120 and the sensor channel 130 and across the sensor 150. The sensor 150 reacts with the fluid to generate the electrical sensor signal indicative of a characteristic of the biological fluid. The fluid continues through the sensor channel 130 and the outlet port 132 whereupon it exits the housing 100 of the tissue interface device 10.

Figure 4:
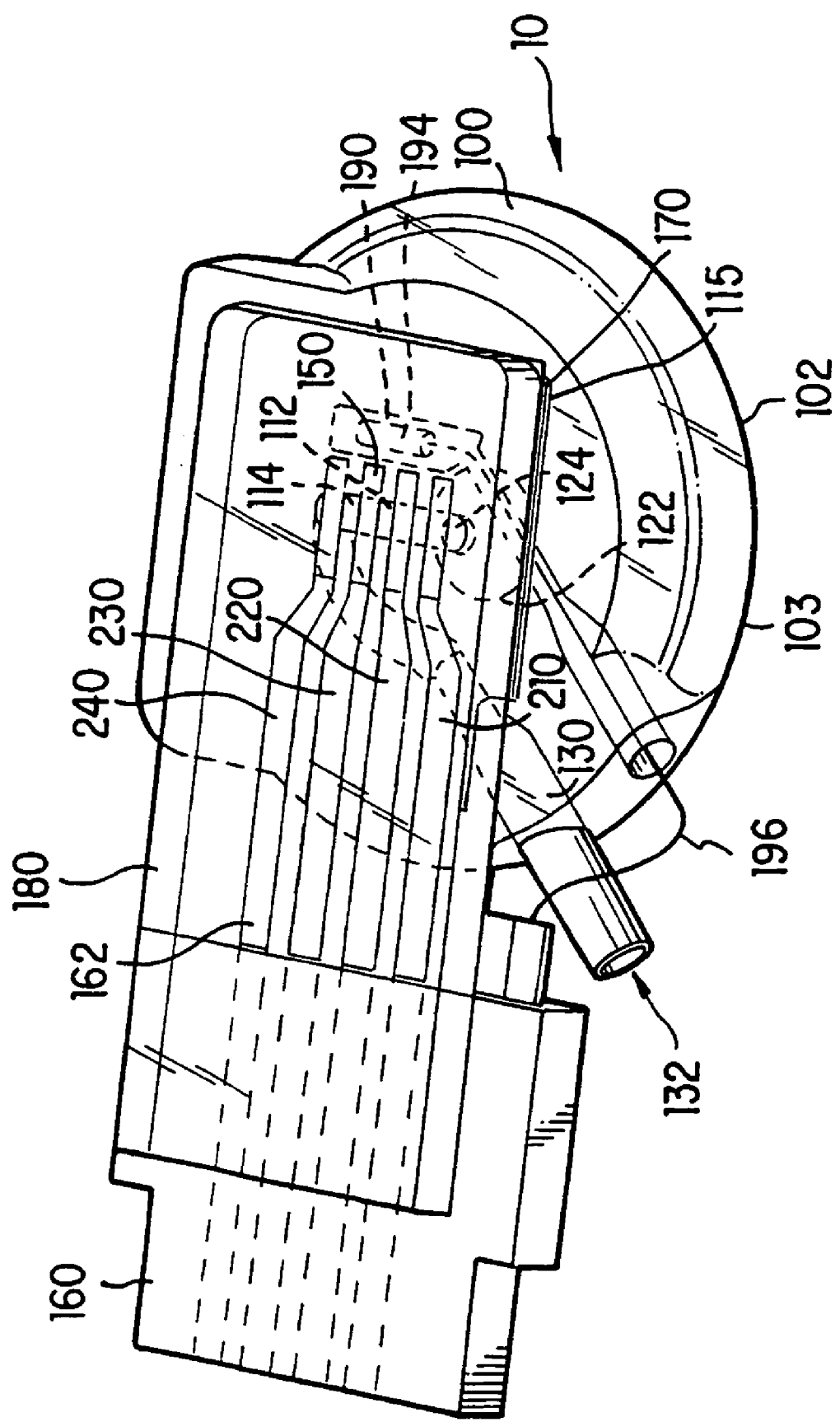
FIG. 4 is a perspective view of the tissue interface device showing a sensor channel, a sensor, and an electrical lead line connecting the sensor and an electrical connector.
Figure 5:
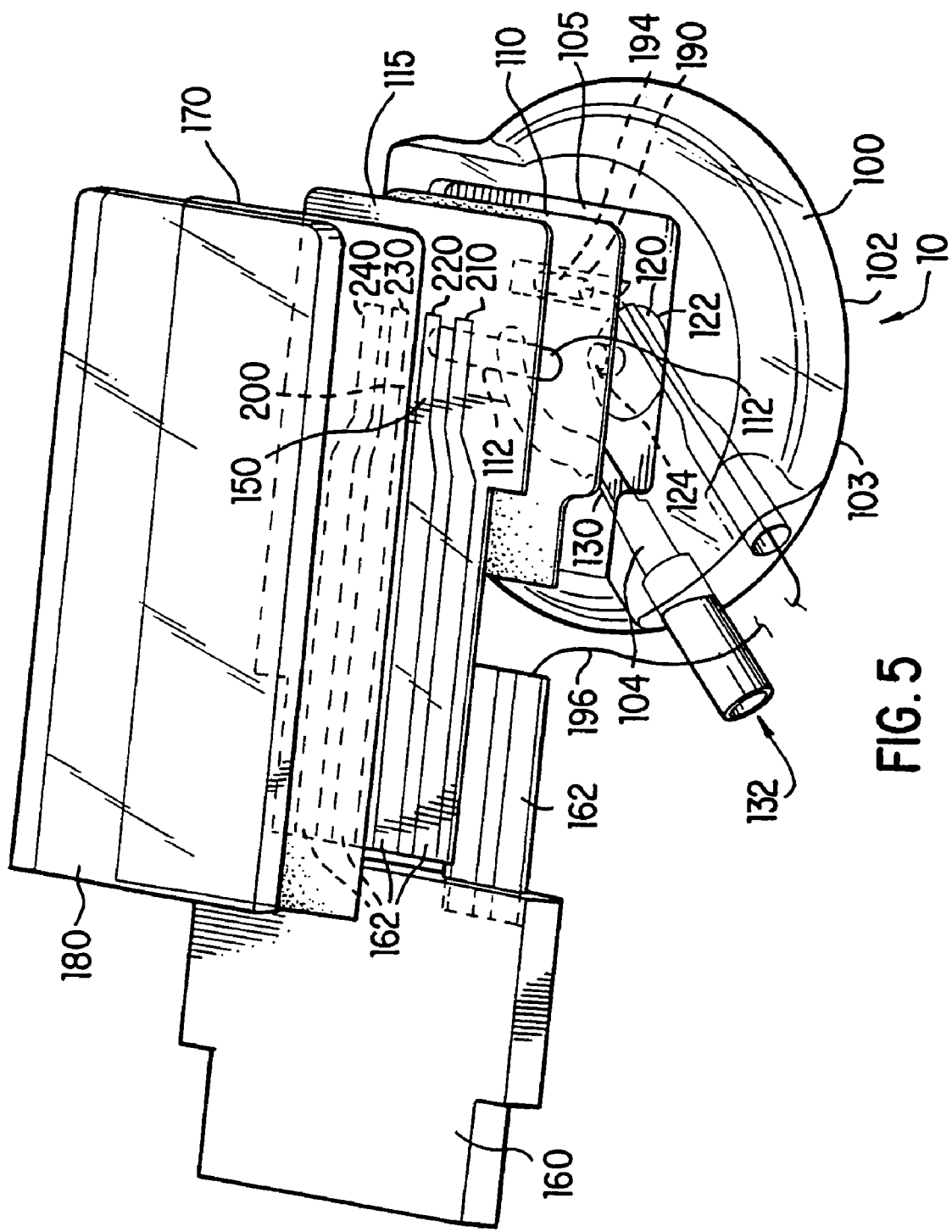
FIG. 5 is an exploded perspective view of the tissue interface device of FIG. 4.
Figure 6:
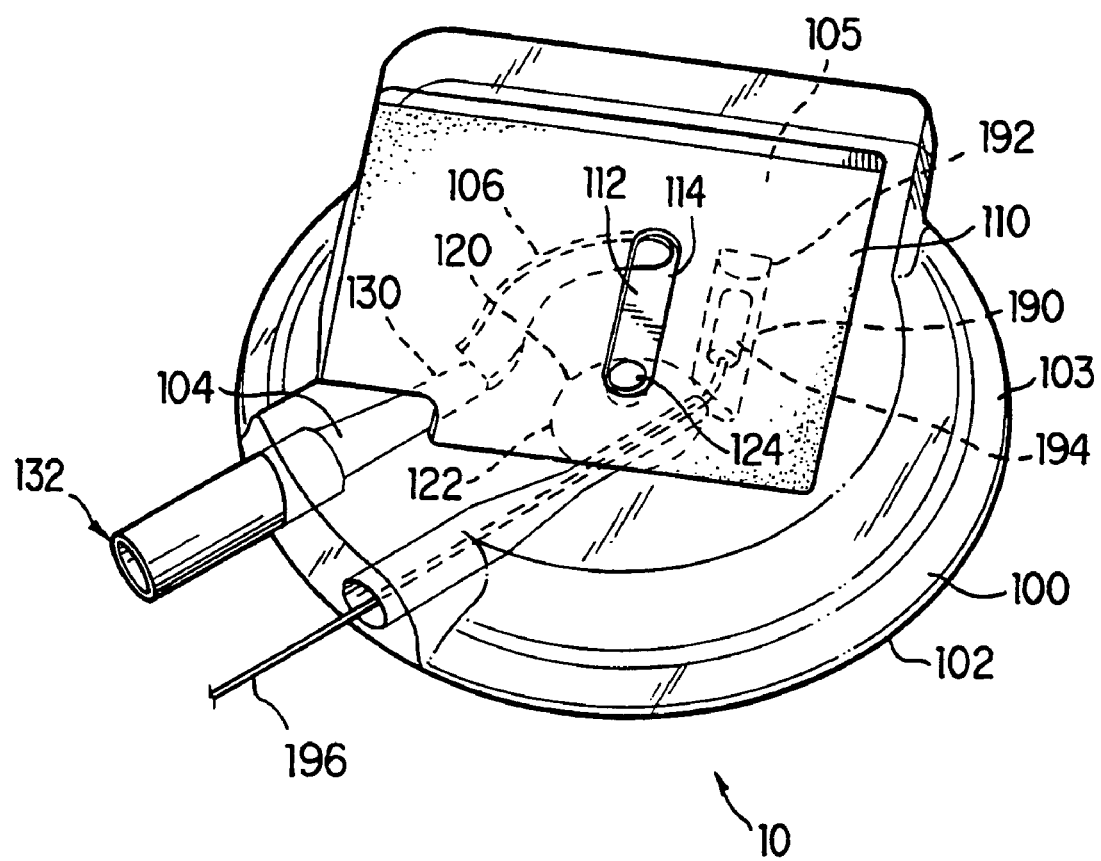
FIG. 6 is a partial perspective of the tissue interface device of FIG. 4 showing a housing and a well-forming adhesive layer.

Referring now to the particular embodiment shown in FIGS. 4–6, the housing 100 of the tissue interface device 10 comprises a body 103, a well-forming adhesive layer 110, and a sensor member 115. The body 103 has a passage 104 extending therein that forms a first portion of the sensor channel 130. The proximal end of the passage 104 forms the outlet port 132 of the housing 100. The body 103 also has a body surface 105 that has a groove 106 therein. The body surface 105 also defines the distal end 124 of the orifice 120. The distal end of the passage 104 is connected to the proximal end of the groove 106.

The body 103 provides structural support to the tissue interface device 10 and in combination with the well-forming adhesive layer 110, serves as the interface between the fluid source and the sensor 150. Any suitable material may be used for the body 103 of the housing 100. Example suitable materials include acrylic, polyester, plastic, ceramic, polycarbonate and polyvinylchloride.

The well-forming adhesive layer 110 has a top surface, an opposing bottom surface and defines an opening 112 or channel cut through the well-forming adhesive layer 110. At least a portion of the bottom surface of the well-forming adhesive layer 110 is connected to a portion of the body surface 105 so that it overlies the groove 106. The well-forming adhesive layer 110 is positioned relative to the body surface 105 so that a portion of the opening 112 of the well-forming adhesive 110 overlies a portion of the body surface 106 to form a well 114. The well 114 is connected to a distal end of the groove 106 of the body surface 105 (by, for example, a portion of the opening 112 of the well-forming adhesive layer 110 overlying the distal end of the groove 106) and is in fluid communication with the distal end of the orifice 120.

The well-forming adhesive layer 110 forms the well 114 to limit the volume of fluid exposed to the sensor 150. Suitable materials for the well-forming adhesive layer 110 are compatible with the fluid of interest, provide adhesive support to the sensor member 115, and are thick enough to provide a well 114 from a opening 112 or channel cut into the well-forming adhesive layer 110. For example, the well-forming adhesive layer 110 may be formed from a layer of pressure sensitive adhesive. In another example, if the fluid of interest is blood or interstitial fluid, the well-forming adhesive layer 110 may be constructed from adhesive-like materials that are not water-soluble.

The sensor member 115 is provided to completely form the sensor channel 130 and to place the sensor 150 in the flow path of the fluid exiting the distal end 124 of the orifice 120. The sensor member 115 has a lower surface upon which is mounted the sensor 150. A portion of the lower surface of the sensor member 115 is connected to the top surface of the well-forming adhesive layer 110 so that at least a portion of the sensor 150 overlies the well 114. As one skilled in the art will appreciate, by the layered application of the well-forming adhesive layer 110 and the sensor member 115, the groove 106 and the well 114 are effectively enclosed to form a second portion of the sensor channel 130 that is in fluid communication with the distal end 124 of the orifice 120. It will be further appreciated that the second portion of the sensor channel 130 is operatively connected to the first portion of the sensor channel 130 to form the sensor channel 130 of the housing 100. The sensor member 115 may be of any thickness effective to provide support and bind the sensor 150.

Moreover, to provide support for the sensor member 115 and to protect the sensor 150 from damage, the housing 100 may further comprise an adhesive bonding layer 170 and a support member 180. The adhesive bonding layer 170 binds the support member 180 to the upper surface of the sensor member 115. The material of construction and dimension of the adhesive bonding layer 170 is not critical to the present invention, thereby allowing any effective adhesive to be used. The support member 180, like the body 103, provides structural support to the sensor member 115 and the sensor 150. To minimize expense, the support member 180 may be constructed of the same material or compatible material as the body 103.

As one skilled in the art will appreciate, the sensor channel 130 may be in any position and in any dimension/shape to allow sufficient flow of fluid across the sensor 150 disposed therein. As noted above, the outlet port 132 of the sensor channel 130 is suitable for connection to a vacuum source sufficient to draw the surface of the biological membrane therein the orifice 120 and to draw fluid through the well 114. The vacuum is sufficient to produce fluid from the biological membrane at a site where small holes/porations (microporations) have been made in the tissue. The well 114 serves to expose the sensor 150 to the fluid that is monitored. Therefore, the well 114 is of a dimension that the sensor 150 does not obstruct the flow of fluid.

The housing 100 of the tissue interface device 10 may also have a thermo-well 190 that extends therein the housing 100. The base 192 of the thermo-well 190 is proximate the distal end 124 of the orifice 120 and is in operative receipt of a thermistor 194. The thermistor 194 generates an electrical temperature sensor signal indicative of the temperature of the fluid proximate the distal end 124 of the orifice 120. The thermistor 194 is connected to the electrical connector 160 via a lead 196 for the communication of the temperature sensor signal to the monitor and control unit 20.

A portion of the bottom end 102 of the housing 100 may include adhesive to facilitate attachment of the device to the biological membrane. The adhesive also is useful to form a pneumatic seal on the biological membrane to allow modulation of the of the pressure levels in those areas proximal the artificial openings.

To further reduce imposed erythema and the dead volume within the orifice, the orifice 120 may be tapered. In this embodiment, the tapered orifice 120 has a shaped orifice surface 126 that extends from the inlet port 122 to the distal end 124 of the orifice 120. Portions of the shaped orifice surface 126 may be straight or may be curved in cross-section. For example, the orifice 120 may have a truncated cone shape or a bell curve shape in cross-section. As one skilled in the art will appreciate, other cross-sectional shapes are contemplated in which the slope of the orifice surface generally slopes inwardly from the inlet port 122 to the distal end 124 of the orifice 120 so that the second diameter d of the orifice 120 is less than the first diameter D of the orifice 120. Hence, in this exemplified embodiment, the relative volume of the tapered orifice 120 near the distal end 124 of the orifice 120 is less than the relative volume of the orifice 120 proximate the inlet port 122.

It is contemplated that at least a portion of the orifice surface 126 may be curved in cross-section. For example, a portion of the orifice surface 126 proximate the bottom end 102 of the housing 100 may be curved so that the translation from the bottom end 102 of the housing 100 to the inlet port 122 portion of the orifice 120 is radiused, i.e., cambered, to form a smoothly contoured inner edge 128. The smoothly contoured inner edge 128 and the generally inward slope of the orifice surface 126 minimize erythema onto the biological membrane during operation as the surface of the biological membrane is drawn into contact and is supported by portions of the orifice 120. The outer edge 103 of the bottom end 102 of the housing 100 may also be radiused to further aid in reducing erythema onto the biological surface during operation of the device 10.

In an embodiment where the orifice 120 is tapered, the first diameter D of the inlet port 122 preferably is about 1.0 to about 20.0 mm in diameter and, more preferably, is about 4.0 to about 10.0 mm in diameter. Similarly, the second diameter d of the distal end 124 of the orifice 120 is about 0.33 to about 10.0 mm in diameter and, more preferably, is about 0.75 to about 3.5 mm in diameter. The diameter of distal end 124 of the orifice 120 is sufficiently large to achieve desired target fluid flow rates. The height H of the orifice 120 from the open inlet port 122 to the distal end 124 is about 0.25 to about 7.0 mm and, more preferably, is about 0.5 to about 5.0 mm. Still more preferably, the height H of the orifice 120 is about 1.0 to about 3.0 mm.

Figure 2:
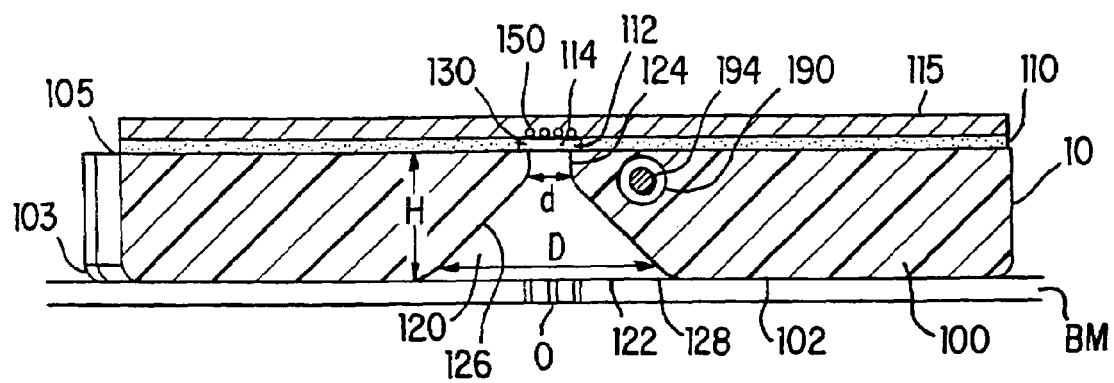
FIGS. 2 and 3 are cross-section views of a tissue interface device through which fluid is collected and a characteristic of the fluid is sensed.
Figure 3:
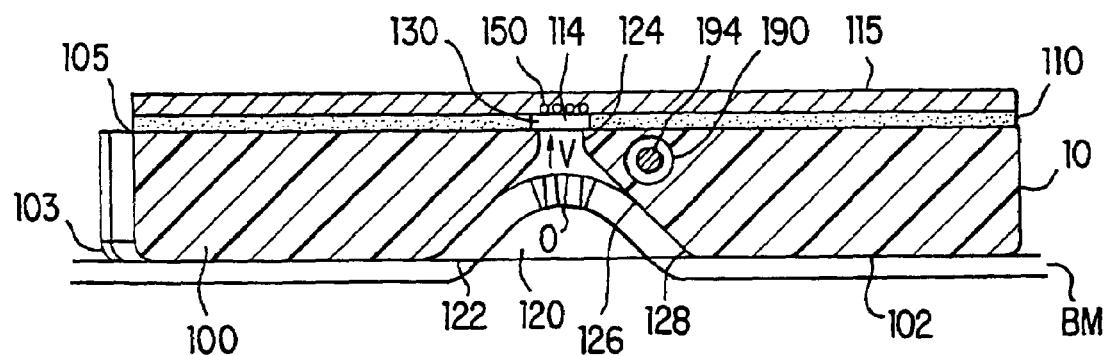

The shape and dimensions of the orifice 120 minimize dead volume and thus minimize time lag. Referring to FIGS. 2 and 3, when the surface of the biological membrane is drawn into the orifice 120 of the housing 110 during the application of a vacuum or a partial vacuum V, the surface of the biological membrane is drawn upwards into the orifice 120 towards the distal end 124 of the orifice 120 and fills a portion of the orifice 120. Thus, the effective dead volume that must be filled with fluid produced from the opening is reduced by the design of the present invention. The general tapered shape and dimensions of the tapered orifice 120 embodiment allow for a stretching of the surface of the biological membrane which may increase the effective pore size of the artificial openings in the biological membrane. By increasing the effective pore size, continuous and or discrete fluid flow rates may be more readily maximized and/or maintained at a constant level for extended periods of time. For example, the application of the vacuum to a skin surface results in a stretching of the skin that may increase the effective pore size of the capillary wall and intervening interstitial spaces which may provide additional access to sources of interstitial fluid.

The sensor 150 of the present invention may be one of any number of known types of sensors, including, but not limited to, an electrochemical biosensor, reactive enzyme based, reflectance, calorimetric, absorbance, fluoresence intensity, or fluorescence lifetime based. Biosensors, such as, for example, an analyte biosensor, may be utilized to detect any number of characteristics contained in the withdrawn fluid, including, but not limited to, detecting: glucose, vitamins (for example, A, C, $B_6$, E, $B_{12}$, etc.), CO2, lactic acid, or other analyte. One or more sensors 150 may be positioned therein the sensor channel 130.

For example, and as shown in FIG. 5, the sensor may comprise a plurality of electrodes 200. Electrode 210 is a working electrode, electrode 220 is a working electrode, electrode 230 is a reference electrode and electrode 240 is a counter-electrode. At least one of the working electrodes 210 and 220 may be coated by a reactant. The electrodes 200 are disposed on the sensor member 115 using screen-printing, pad printing, sputter coating, photolithography or other suitable techniques, using known inks and dialectrics.

Each working electrode 210 and 220 may be made from a variety of materials such as carbon and metals such as gold or silver. For example, each working electrode 210 and 220 may be made from catalytic metals such as platinum, palladium, chromium, ruthenium, rubidium, or mixtures thereof.

In the exemplified electrode sensor 150 discussed above, in order to detect and/or measure the level of an analyte or desired characteristic present in a fluid, at least one working electrode and at least one reference electrode are necessary. However, more than one working electrode and one or more counter-electrodes may also be present. For example, the working electrode 210 may not contain the reactant and will therefore produce an electrical signal that is indicative of the fluid without an analyte. This allows reduction or elimination of the signal due to various interferent compounds by subtracting the electrical signal of the working electrode 210 from the electrical signal of the working electrode 220.

Alternatively, one working electrode may be used if the levels of interference are not significant.

The reference electrode 230 establishes a potential relative to the fluid. The reference electrode 230 may, for example, contain silver/silver-chloride. The counter-electrode 240, which is optional, serves to ground the current generated by the working electrodes 210 and 220. For simplicity, the counter-electrode 240 may contain the same materials as the working electrodes 210 and 220. The exemplified sensor 150 may contain more than one working electrode, more than one reference electrode and more than one counter-electrode, as is well known in the art.

The active surface of the electrodes 200 may be any shape and dimension to effectively operate. Particularly, the surface area of any of the electrodes 200 can be varied as long as there is sufficient sensitivity to measuring the current. For example, the electrodes 200 in the exemplified sensor 150 have active surface areas between 0.1 mm$^2$ and 10 mm$^2$. Preferably, the electrodes 400 have a surface area of about 1 mm$^2$.

As noted above, the sensor 150 is connected to the electrical lead line 162 that terminates in the electrical connector 160 for coupling to the remote monitor and control unit 20. In the exemplified sensor 150, the electrical lead lines 162 that couple the electrodes 200 to the connector 160 may be traces of graphite or silver/silver-chloride. However, other conductive material such-as-gold or tin are suitable to connect the electrodes 200 to the connector 160. These traces could be applied via any method that provides a sufficient resolution such as ink-jet printing or pad printing. In addition, the printed traces could be replaced with traditional connection techniques.

Figure 7:
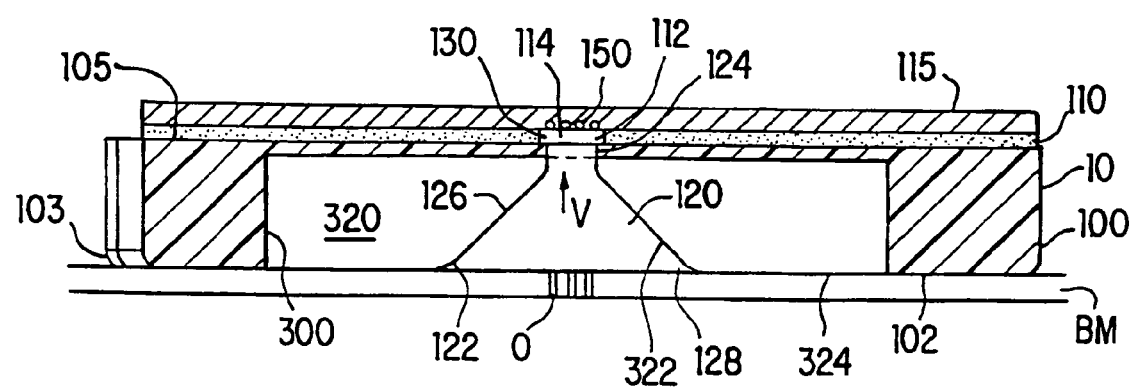
FIG. 7 is a cross-section view of a tissue interface device featuring a flexible insert.

Further reductions in dead volume and time delay may be achieved through the incorporation of a flexible skin interface which can adapt to variations in skin distension between patients. Variations in dead volume and hence time lag occur due to variation in the distension of an organism's biological membrane. In addition, the distension may vary over time on the same organism. Referring to FIG. 7, an alternate embodiment of the tissue interface device 10 is shown. This embodiment includes a notch 300 and a flexible insert 320. The notch 300 is formed in the bottom end 102 of the housing 100 and opens out to the portion of the orifice 120 proximate the distal end 124 of the orifice 120. The flexible insert 320 has a chamber 322 extending therethrough, a base surface 324 and is shaped to be complementarily received within the notch 300. When the flexible insert 320 is received therein the notch 300, the base surface 324 of the flexible insert 320 is coplanar to a portion of the bottom end 102 of the housing 100 and the chamber 322 and the portion of the orifice 120 embodied in the housing 100 form the orifice 120 of the tissue interface device 10. As illustrated in FIG. 7, the chamber 322 may be shaped so that the orifice 120 is tapered.

In operation, this embodiment of the tissue interface device 10 is positioned on a site overlying one or more artificial openings in the biological membrane. When positioned, the orifice 120 of the housing 100 is positioned in fluid communication with fluid produced from the artificial opening formed in the biological membrane. Fluid enters the tissue interface device 10 through the inlet port 122. Under application of vacuum at the outlet port 132, the surface of the biological membrane is drawn therein the orifice 120 and into contact with the surface of the flexible insert 320 (i.e., into contact with the shaped orifice surface 126 of the orifice 120) which resiliently molds itself to closely conform to the surface condition of the biological membrane. Because the space between the surface of the biological membrane and the shaped orifice surface 126 is reduced, effective dead volume and hence the time delay is reduced.

Also, due to the resilient nature of the flexible insert 320, a resistive force is produced which acts on the surface of the biological membrane to reduce the erythema imposed by the tissue interface device 10. Suitable materials for the flexible insert 320 are flexible enough to allow the biological membrane to distend against it to an acceptable degree of compression. Example suitable materials include silicone rubber, urethane, and pliable polymers.

Further in operation, the fluid is drawn from the artificial opening within the biological membrane into the orifice 120 and hence into the sensor channel 130 and across the sensor 150. The sensor 150 reacts with the fluid to generate the electrical sensor signal indicative of a characteristic of the biological fluid. The fluid continues through the sensor channel 130 and the outlet port 132 whereupon it exits the housing 100 of the tissue interface device 10. Thus, this embodiment of the tissue interface device 10 incorporates all of the advantages of the first embodiment described immediately above while beneficially further reducing dead volume, time lag, and imposed erythema.

Figure 8:
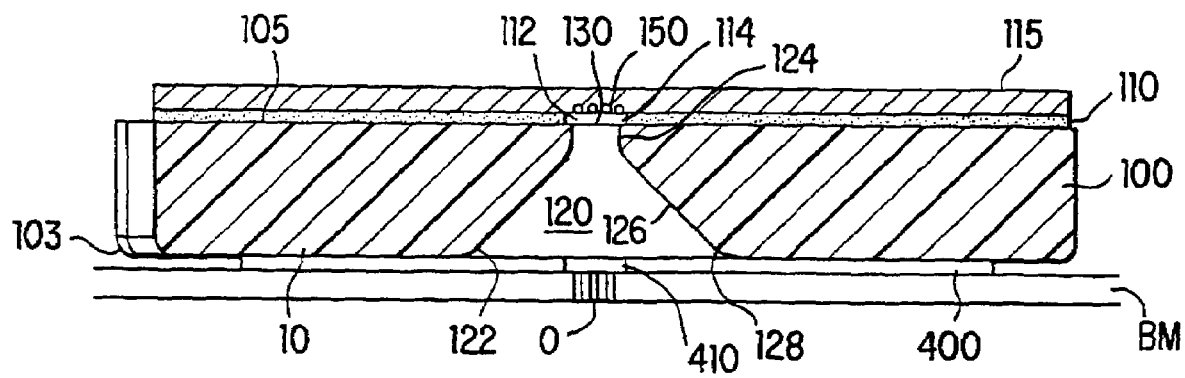
FIGS. 8 and 9 are cross-section views of a tissue interface device featuring a flexible membrane having an opening in fluid communication with the artificial openings in the biological membrane and the sensor channel.
Figure 9:
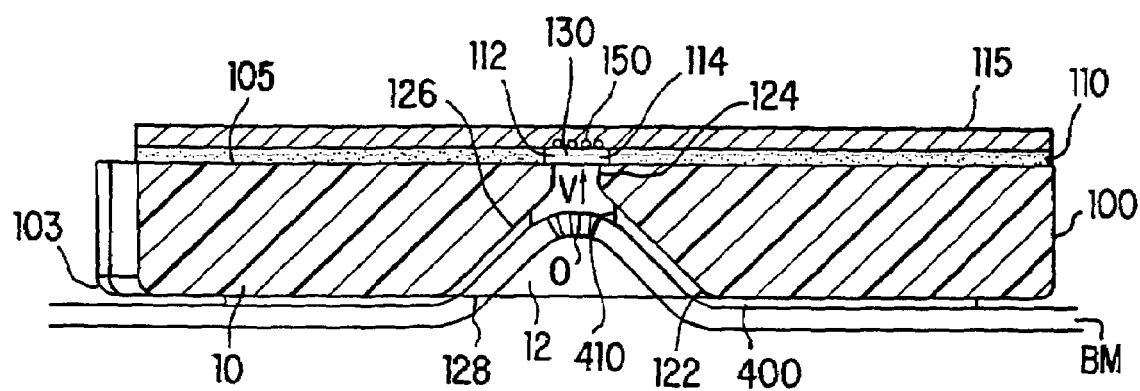

Referring now to FIGS. 8 and 9, a variation of the tissue interface device 10 is shown in which an opening 410 in a flexible membrane 400 opens into the inlet port 122 of the housing 100. The opening 410 extends therethrough the membrane 400 and has a diameter less than the diameter of the inlet port 122 of the orifice 120. A portion of the surface of the flexible membrane 400 is affixed, for example, by use of a pressure sensitive adhesive, to the bottom end 102 of the housing 100. The flexible membrane 400 is positioned so that the opening 410 of the flexible membrane 400 is positioned approximately opposed to the inlet port 122 of the housing 100.

In operation, this embodiment of the tissue interface device 10 is positioned on a site overlying one or more artificial openings in the biological membrane. To form a pneumatic seal on the biological membrane to allow modulation of the pressure levels in those areas proximal the artificial openings and to facilitate attachment of the device 10 to the biological membrane, at least a circumferential portion of the flexible membrane 400 and/or the bottom end 102 of the housing 100 may include adhesive. When positioned, the opening 410 of the flexible membrane 400 and the orifice 120 of the housing 100 are positioned in fluid communication with fluid produced from the artificial opening formed in the biological membrane. Fluid enters the tissue interface device 10 through the opening in the flexible membrane 400 and is drawn into the interior of the orifice 120. Under application of vacuum at the outlet port 132, the surface of the biological membrane is drawn into contact with the flexible membrane 400 and the flexible membrane 400 and the biological membrane are drawn into the interior of the orifice 120. The flexible membrane 400 is placed into contact with the shaped orifice surface 126 of the orifice 120 and resiliently molds itself to closely conform to the surface condition of the biological membrane and the shaped orifice surface 126. The orifice 120 may be tapered as previously described.

Because the space between the surface of the biological membrane and the flexible membrane 400 is reduced, effective dead volume and hence the time delay is reduced. The fluid expressed from the artificial opening is drawn through the tissue interface device 10 as described in the embodiments above. Thus, similar to the embodiment described immediately above, this embodiment of the tissue interface device incorporates all of the advantages of the first embodiment while beneficially further reducing dead volume, time lag, and imposed erythema.

As noted for the embodiment described above, a resistive force is produced by the resilient nature of the flexible membrane 400 which acts on the surface of the biological membrane to reduce the erythema imposed by the tissue interface device 10. Suitable materials for the flexible membrane 400 are flexible enough to allow the biological membrane to distend against it to an acceptable degree of compression, provide an degree of elongation which allows the flexible membrane 400 to stretch under the applied suction force, and are thick enough to provide to conform to the surface of the biological membrane. Suitable materials preferably have an elongation rating from about 125% to 350%, and more preferably, from about 175% to 225%; and a thickness from about 0.2 mm to about 2.5 mm, and more preferably, from about 0.5 mm to 1.5 mm. Example suitable materials include a polymer film, a polyester film, a polyethylene film and a polyolefinic film.

Figure 10:
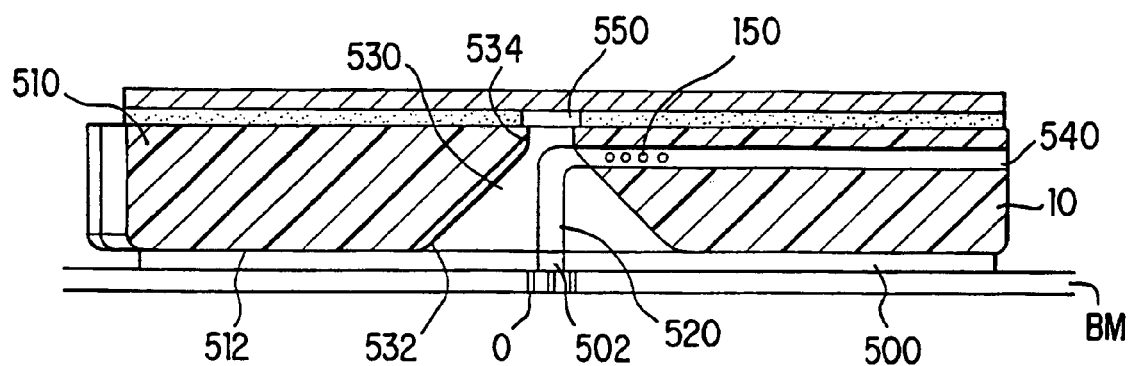
FIGS. 10 and 11 are cross-section views of a tissue interface device having a vacuum channel and a sensor channel and featuring a gas permeable flexible membrane having an opening connected to a flexible tube which is connected to the sensor channel.
Figure 11:
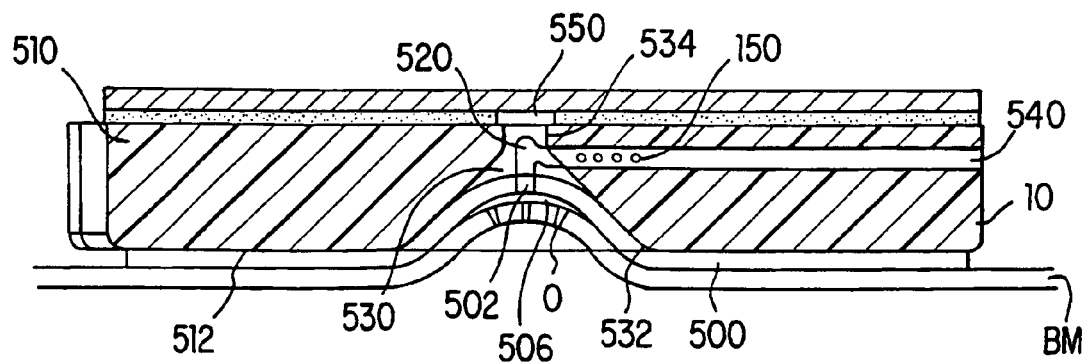

FIGS. 10–11 shown another embodiment of a tissue interface device 10 which has a flexible membrane 500 for beneficially reducing dead volume, time lag, and imposed erythema. This embodiment includes a housing 510, a flexible membrane conduit 520, and the flexible membrane 500. The housing 510 has a orifice 530 that extends therein from an open inlet port 532 on the bottom end 512 of the housing 510 and terminates in a distal end 534. The housing 510 also includes a sensor channel 540 and a vacuum channel 550 that may be suitably coupled to the vacuum source 30. The vacuum channel 550 is in fluid communication with the distal end 534 of the orifice 530.

The flexible membrane 500 has a top surface, a bottom surface, and an opening 502 that extends therethrough the membrane 500. The opening 502 of the flexible membrane 500 is less than the diameter of the inlet port 532 of the orifice 530. At least a portion of the top surface of the flexible membrane 530 is connected to the bottom end 512 of the housing 510, such as, for example, by a circumferentially extending ring of adhesive. Suitable materials for the flexible membrane 500 are flexible enough to allow the flexible membrane 500 to provide an degree of elongation which allows the flexible membrane 500 to stretch under the applied suction force and are gas permeable. An example suitable material is a flexible hydrophobic gas permeable polymer film, such as Hydrolon, produced by Pall Specialty Materials, Port Washington, N.Y.

The flexible conduit 520 is connected to, and in fluid communication therewith, an inlet end of the sensor channel 540 and the opening 502 in the flexible membrane 500. Thus, the top surface of the flexible membrane 500, the exterior of the flexible conduit 520, and the orifice 530 form an enclosed void that is in communication with the vacuum channel 550 so that at least a portion of the top surface of the flexible membrane 500 is in fluid communication with the vacuum source 30.

In operation, this embodiment of the tissue interface device 10 is positioned on a site overlying one or more artificial openings in the biological membrane. At least a circumferential portion of the bottom surface of the flexible membrane 500 may include adhesive to form a pneumatic seal on the biological membrane to allow modulation of the pressure levels in those areas proximal the artificial openings and to facilitate attachment of the device 10 to the biological membrane. When positioned, at least a portion of the bottom surface of the flexible membrane 500 is positioned in temporarily sealed contact with the biological membrane around the artificial opening so that the opening 502 of the flexible membrane 500 is in fluid communication with the artificial opening. Fluid enters the tissue interface device 10 through the opening 502 in the flexible membrane and is drawn into the flexible conduit 520 upon application of vacuum to the outlet port of the sensor channel 540. Under application of vacuum to the vacuum channel 550, the top surface of the flexible membrane 500 is drawn into the interior of the orifice 530 and the bottom surface of the flexible membrane is pulled fractionally away from the surface of the biological membrane which creates a gap 506. Fluid flows into the gap 506, and through the applied suction and/or capillary action, the fluid passes through the opening 502 of the flexible membrane 500 into the flexible conduit 520 and therethrough the sensor channel 540 to pass the sensor 150. Because the volume between the surface of the biological membrane and the sensor 150 is reduced, effective dead volume and hence the time delay is reduced. Thus, this embodiment of the tissue interface device 10 incorporates all of the advantages of the first embodiment while beneficially further reducing dead volume, time lag, and for beneficially providing a degassed sample of fluid to the sensor 150.

It should be understood that the preceding is merely a detailed description of various embodiments of this invention and that numerous changes to the disclosed embodiments can be made in accordance with the disclosure herein without departing from the spirit or scope of the invention. The preceding description, therefore, is not intended to limit the scope of the invention. Rather, the scope of the invention is to be determined only by the appended claims and their equivalents.

What is claimed is:

1. A tissue interface device for positioning about an artificial opening in a biological membrane to measure tissue characteristics, comprising:
    a. a housing having a bottom end,
    b. at least one sensor, and
    c. a sensor channel, wherein, within the housing, the sensor channel couples the bottom end with the sensor
    d. wherein the housing defines an orifice extending into the housing, the orifice having an open inlet port on the bottom end of the housing to receive liquid and a distal end that is in fluid communication with the sensor channel and wherein a portion of the bottom end of the orifice is radiused.

2. The tissue interface device of claim 1, wherein the sensor is positioned in the sensor channel that is in fluid communication with the sensor channel for sensing a characteristic of fluid flowing from the artificial opening in the biological membrane, and whereby, in use, the orifice is in fluid communication with the artificial opening in the biological membrane.

3. The tissue interface device of claim 1, wherein the inlet port has a first diameter and the distal end has a second diameter.

4. The tissue interface device of claim 3, wherein the orifice is tapered and wherein the second diameter is less than the first diameter.

5. The tissue interface device of claim 4, wherein the orifice has a bell-shaped curve in cross-section.

6. The tissue interface device of claim 4, wherein the orifice has a shaped orifice surface that extends from the inlet port to the distal end of the orifice, and wherein at least a portion of the orifice surface is curved in cross-section.

7. The tissue interface device of claim 1, wherein the sensor channel has an outlet port to discharge fluid.

8. The tissue interface device of claim 7, wherein the outlet port is suitable for connection to a vacuum source.

9. The tissue interface device of claim 1, wherein the sensor generates a signal representing a characteristic of the biological fluid.

10. The tissue interface device of claim 1, wherein the sensor generates an electrical sensor signal representing a characteristic of the biological fluid.

11. The tissue interface device of claim 10, further comprising an electrical connector and an electrical lead line in operative communication with the sensor, the electrical lead line coupling the electrical sensor signal to the electrical connector.

12. The tissue interface device of claim 11, wherein the electrical connector is coupled to a monitor and control unit.

13. The tissue interface device of claim 1, wherein the housing is disposable.

14. The tissue interface device of claim 1, wherein, in use, at least a portion of the bottom end of the housing is positioned in sealed contact with the biological membrane around the artificial opening.

15. The tissue interface device of claim 1 wherein the housing has a notch extending therein, wherein the housing further comprises a flexible insert having a base surface, the flexible insert shaped to be complementarily received within the notch so that the base surface forms a portion of the bottom end of the housing, and wherein the flexible insert includes at least a portion of the orifice.

16. The tissue interface device of claim 1, wherein the sensor is adapted for continuously assaying fluid flowing from the artificial opening.

17. The tissue interface device of claim 1, wherein the sensor is positioned proximate the distal end of the orifice.

18. A tissue interface device for positioning about an artificial opening in a biological membrane to measure tissue characteristics, comprising:
  a. a housing having a bottom end,
  b. at least one sensor, and
  a sensor channel, wherein, within the housing, the sensor channel couples the bottom end with the sensor and wherein the housing defines an orifice extending into the housing, the orifice having an open inlet port on the bottom end of the housing to receive liquid and a distal end that is in fluid communication with the sensor channel and wherein the housing comprises:
    a) a body having a passage and a body surface having a groove therein, the passage forming a first portion of the sensor channel which includes an outlet port, wherein the passage is connected to a proximal end of the groove, and wherein the distal end of the orifice is defined on the body surface of the body,
    b) a well-forming adhesive layer having a top surface and an opposing bottom surface and defining an opening extending therethrough, wherein at least a portion of the bottom surface of the well-forming adhesive layer is connected to the body surface and overlies the groove of the body surface, wherein a portion of the opening of the well-forming adhesive layer overlies a portion of the body surface to form a well, the well connected to a distal end of the groove of the body surface and in fluid communication with the distal end of the orifice, and
    c) a sensor member having a lower surface, wherein the sensor is mounted to the lower surface of the sensor member, and wherein a portion of the lower surface of the sensor member is connected to the top surface of the well-forming adhesive layer so that at least a portion of the sensor overlies the well, wherein the groove and the well are enclosed to form a second portion of the sensor channel that is in fluid communication with the first portion of the sensor channel and the distal end of the orifice.

19. The tissue interface device of claim 18, wherein the sensor member has a upper surface, and wherein the housing further comprises an adhesive bonding layer and a support member, wherein the adhesive bonding layer is connected to the upper surface of the sensor member, and wherein the support member is fixedly connected to adhesive bonding layer.

20. The tissue interface device of claim 18, wherein at least a portion of the opening of the adhesive layer overlies the distal end of the orifice.

21. A tissue interface device for positioning about an artificial opening in a biological membrane to measure tissue characteristics, comprising:
  a. a housing having a bottom end,
  b. at least one sensor, and
  c. a sensor channel, wherein, within the housing, the sensor channel couples the bottom end with the sensor
  d. an electrical connector and an electrical lead line in operative communication with the sensor, the electrical lead line coupling the electrical sensor signal to the electrical connector and wherein the sensor generates an electrical sensor signal representing the characteristic of the biological fluid
and wherein the housing has a thermo-well extending therein, the thermo-well having a base that is proximate the distal end of the orifice, and further comprising a thermistor positioned in the thermo-well proximate the base of the thermo-well, wherein the thermistor is connected to the electrical connector.

22. A tissue interface device for positioning about an artificial opening in a biological membrane to measure tissue characteristics, comprising:
  a. a housing having a bottom end,
  b. at least one sensor, and
  a sensor channel, wherein, within the housing, the sensor channel couples the bottom end with the sensor
and wherein the housing defines an orifice extending into the housing, the orifice having an open inlet port on the bottom end of the housing to receive liquid and a distal end that is in fluid communication with the sensor channel and
wherein the inlet port has a first diameter and the distal end has a second diameter and wherein the orifice is tapered and wherein the second diameter is less than the first diameter and wherein the orifice has a shaped orifice surface that extends from the inlet port to the distal end of the orifice, and wherein at least a portion of the orifice surface is curved in cross-section and
wherein a portion of the shaped orifice surface of the orifice proximate the bottom end of the housing is curved so that the transition from the bottom end of the housing to the inlet port of the orifice is radiused.

23. A tissue interface device for positioning about an artificial opening in a biological membrane of an organism and for coupling to a monitor and control unit and a vacuum source, comprising:
  a) a housing having a bottom end, a sensor channel, a vacuum channels, and a sensor, wherein the housing defines an orifice extending therein the housing, the orifice having an open inlet port on the bottom end of the housing and a distal end that is in fluid communication with the vacuum channel, and wherein the sensor channel and the vacuum channel are for fluid communication with the vacuum source, b) a flexible membrane having a top surface, a bottom surface, and an opening extending therethrough, wherein the opening in the flexible membrane has a diameter less than the first diameter of the inlet port of the orifice, wherein at least a portion of the top surface of the flexible membrane is connected to the bottom end of the housing so that the opening of the flexible membrane is positioned near the inlet port of the orifice, wherein at least a portion of the top surface of the flexible membrane is in fluid communication with the vacuum source, and wherein, in use, at least a portion of the bottom surface of the flexible membrane is positioned in sealed contact with the biological membrane around the artificial opening so that the opening of the flexible membrane is in fluid communication with the artificial opening in the biological membrane and with the inlet port of the orifice, and c) a flexible conduit connected to, and in fluid communication therewith, the sensor channel and the opening in the flexible membrane, wherein the sensor is positioned in the sensor channel in fluid communication with the flexible conduit for sensing a characteristic of fluid flowing from the artificial opening in the biological membrane, and wherein the flexible membrane is a gas permeable membrane.

24. The tissue interface device of claim 23, wherein the orifice is tapered, and wherein the inlet port has a first diameter and the distal end has a second diameter that is less than the first diameter.

25. The tissue interface device of claim 23, wherein the sensor is positioned proximate the distal end of the orifice.

26. A tissue interface device for positioning about an artificial opening in a biological membrane to measure tissue characteristics, comprising:

a. a housing having a bottom end, b. an orifice in the housing, the orifice having an open inlet port on the bottom end of the housing to receive liquid from the tissue and a distal end c. a sampling channel within the housing the channel being in fluid communication with the distal end; and d. a fluid permeable flexible membrane is connected to the bottom end of the housing so that the opening of the flexible membrane is positioned near the inlet port of the orifice, wherein, in use, at least a portion of the flexible membrane is positioned in temporarily sealed contact with the biological membrane and around the biological membrane.

* * * * *